United States Patent [19]
Koenig et al.

[11] 4,003,938
[45] Jan. 18, 1977

[54] MANUFACTURE OF ALIPHATIC ISOCYANATES

[75] Inventors: Karl-Heinz Koenig, Frankenthal; Siegfried Kersten, Ludwigshafen; Christian Reitel, Heidelberg, all of Germany

[73] Assignee: BASF Aktiengesellschaft, Ludwigshafen (Rhine), Germany

[22] Filed: Mar. 4, 1976

[21] Appl. No.: 663,968

[30] Foreign Application Priority Data

Mar. 21, 1975 Germany .......................... 2512514

[52] U.S. Cl. ............................................ 260/453 P
[51] Int. Cl.$^2$ ...................................... C07C 118/00
[58] Field of Search ............................... 260/453 P

[56] References Cited

UNITED STATES PATENTS

| | | | |
|---|---|---|---|
| 3,734,941 | 5/1973 | Sydor | 260/453 P |
| 3,919,280 | 11/1975 | Rosenthal et al. | 260/453 P |

*Primary Examiner*—Lewis Gotts
*Assistant Examiner*—Dolph H. Torrence
*Attorney, Agent, or Firm*—Johnston, Keil, Thompson & Shurtleff

[57] ABSTRACT

Aliphatic isocyanates are produced by thermal decomposition of the corresponding β-naphthyl carbamates.

3 Claims, No Drawings

MANUFACTURE OF ALIPHATIC ISOCYANATES

This invention relates to a process for the manufacture of aliphatic isocyanates of the general formula I $$R - N = C = O \qquad \text{I}$$

in which R denotes straight-chain or branched-chain alkyl of from 1 to 10 carbon atoms or alkenyl of from 2 to 6 carbon atoms, by thermal decomposition (pyrolysis) of the corresponding N-alkyl or N-alkenyl β-naphthyl carbamates.

The synthesis of isocyanates by thermal decomposition of ureas or urethanes is known (Houben-Weyl, Methoden der organischen Chemie, vol. 8, page 126 (1952)).

Suitable ureas for pyrolysis are trisubstituted ureas having not more than 2 aryl groups (German Patent 748,714), provided that the two amide groups of the urea used are derived from amines having markedly different boiling points.

Annalen der Chemie 562, 205 (1949) describes the manufacture of isocyanates by decomposition of o-hydroxyaryl urethanes. Heating of the reaction product of pyrocatechol carbonate and ethylamine at 210° C produces ethyl isocyanate, which is obtained, however, in a yield of only 40 to 55% of theory.

In a process described in U.S. Pat. No. 3,076,007, saturated aliphatic isocyanates may be synthesized by thermal decompositon of 2-hydroxyethyl N-alkyl carbamates at temperatures ranging from 100° to 300° C and at reduced pressure.

Here the separation of the dissociation products presents difficulties. Separation of isocyanate and ethylene glycol by distillation is only successful when the boiling points differ by an adequate amount. When the boiling point of the isocyanate is near that of ethylene glycol, as is mainly the case with alkyl isocyanates having from 3 to 5 carbon atoms, the dissociation products must be condensed together and the distillate immediately quenched in order to prevent recombination to the carbamate. The distillate must then be diluted with a water-immiscible inert solvent and the ethylene glycol removed by repeated extraction with water. The presence of ethylene glycol in the isocyanates would lead to recombination to carbamates during further processing of the isocyanates.

The yield obtained is very low, being only 23% in the case of butyl isocyanate even when decomposition is carried out in the presence of a basic catalyst, as is recommended in the citation for increasing the yield.

U.S. Pat. 1,247,451 also recommends effecting thermal decomposition of urethanes in the presence of a catalyst in order to obtain good yields. In this case the addition of Lewis acids is proposed. Other disadvantages of this process are the very high pyrolysis temperature of from 400° to 600° C and the low yield of pure monoisocyanate.

It is also known, from J. Amer. Chem. Soc., 81, 2138 (1959), that urethanes of secondary and tertiary alcohols having hydrogen atoms in the β-position may be thermally decomposed with cis-elimination to form amine, carbon dioxide and alkylene.

It is an object of the invention to provide a method of synthesizing isocyanates in which no condensation reactions and side reactions occur and in which the pyrolysis products are easy to separate, the urethane used in said method being readily available and cheap.

We have now found a process for the manufacture of aliphatic isocyanates of the general formula I $$R - N = C = O \qquad \text{I}$$

in which R denotes straight-chain or branched-chain alkyl of from 1 to 10 carbon atoms or alkenyl of from 2 to 6 carbon atoms, in which process β-naphthyl carbamates of the general formula II

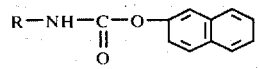

in which R has the above meanings, are thermally decomposed at a temperature of from 150° to 500° C.

Compared with the prior art processes for the manufacture of isocyanates, the process of the invention has considerable advantages.

Very pure products are obtained in high yields after short reaction times and without the use of any catalyst. The boiling points of β-naphthol and the isocyanates formed differ considerably, and separation of the dissociation products is thus easy. The isocyanates are obtained in a purity of more than 97%. The yield exceeds 85% of theory. The recovered β-naphthol may be reused for carbamate synthesis.

Another advantage is the possibility of manufacturing low-boiling isocyanates such as methyl, ethyl, n-proply, isopropyl and t-butyl isocyanates, which are difficult to obtain by other processes.

Decomposition is carried out in a pyrolysis apparatus at a temperature of from 150° to 500° C and preferably from 200° to 350° C. The good thermal stability of β-naphthol makes it possible to use relatively high pyrolysis temperatures, which effect almost quantitative decomposition of the carbamates and consequently give high yields of isocyanate. At the same time, the residence time of the carbamate in the pyrolysis zone is reduced to a few minutes.

It is recommended to carry out decomposition under reduced pressure, preferably a pressure of from 1 to 200 mm of Hg, since this reduces the residence time of the thermally unstable isocyanates in the pyrolysis zone to a minimum.

The N-alkyl and N-alkenyl β-naphthyl carbamates used as starting materials are advantageously obtained by direct reaction of β-naphthol with the corresponding carbamoyl chlorides. Suitable compounds are N-alkyl β-naphthyl carbamates containing straight-chain or branched-chain alkyl of from 1 to 10 carbon atoms and preferably of from 1 to 4 carbon atoms, and N-alkenyl-β-naphthyl carbamates of from 2 to 6 carbon atoms, for example N-methyl, N-ethyl, N-n-propyl, N-iso-propyl, N-n-butyl, N-isobutyl, N-sec-butyl, N-t-butyl, N-2-methylbutyl, N-1,2-dimethyl-n-propyl, N-pentyl, n-1-methyl-n-butyl, N-neopentyl, N-n-hexyl, N-1-methyl-2,2-dimethyl-n-propyl, N-1-n-propyl-n-butyl, N-n-octyl, N-n-decyl, N-vinyl, N-allyl, N-isopropenyl, N-1,1-dimethylallyl, N-1-methyl-1-ethylallyl and N-n-buten-(4)-yl-β-naphthyl carbamates.

EXAMPLE

Manufacture of CH₃NCO 0.5 mole of β-naphthyl-N-methyl carbamate is placed in a 500 ml reaction vessel provided with stirrer, thermometer and reflux condenser. The contents of the apparatus are under reduced pressure (200 mm of Hg). The internal temperature is adjusted to 240° C by means of a bath of molten metal, and the melt is thoroughly stirred at this temperature for 10 minutes. The $CH_3NCO$ eliminated is collected in a cold trap. The yield is 86% of theory. The boiling point is 38° C.

The isocyanates listed in the Table below were also prepared by the process described in the above Example:

TABLE

| Isocyanate | Purity (%) | Yield (%) | Boiling point (° C) |
|---|---|---|---|
| $CH_3$-NCO | 98 | 86 | 38 |
| $CH_3CH_2$-NCO | 97 | 88 | 60 |
| i-$C_3H_7$-NCO | 97 | 86 | 74 |
| n-$C_3H_7$-NCO | 97 | 86 | 88 |
| $CH_2$=CH-$CH_2$-NCO | 98 | 86 | 88 |
| n-$C_4H_9$-NCO | 98 | 85 | 115 |
| t-$C_4H_9$-NCO | 98 | 85 | 85 |
| $CH_3$-C($CH_3$)$_2$-CH($CH_3$)-NCO | 97 | 84 | 58 (13 mm) |
| $CH_3$-$CH_2$-$CH_2$-CH(n-$C_3H_7$)-NCO | 97 | 85 | 40 (12 mm) |

The isocyanates which may be prepared by the process of the invention, preferably methyl, ethyl, n-propyl and isopropyl isocyanates, are valuable starting materials for the manufacture of plant protection agents, insecticides, dyes, synthetic resins and plastic materials, water-repellent finishes for textiles, detergents, bleaches and adhesives. Of particular significance is their conversion to urethanes, for example for use as foams or high molecular weight coatings of high flexibility, or to ureas. For further details on the use of such compounds see Ullmanns -Encyklopaedie der technischen Chemie, vol. 9, pp. 11, 13 and 404 and vol. 17, p. 204.

We claim:

1. A process for the manufacture of aliphatic isocyanates of the general formula I $$R - N = C = O \qquad \text{I}$$

in which R denotes straight-chain or branched-chain alkyl of from 1 to 10 carbon atoms or alkenyl of from 2 to 6 carbon atoms, wherein β-naphthyl carbamates of the general formula II

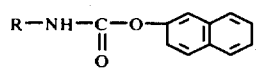

in which R has the meanings stated above, are thermally decomposed at a temperature of from 150° to 500° C.

2. A process as claimed in claim 1, wherein the thermal decomposition is carried out at a temperature of from 200° to 350° C.

3. A process as claimed in claim 1, wherein the thermal decomposition is carried out at a pressure of from 1 to 200 mm of Hg.

* * * * *